United States Patent
Brenner et al.

(10) Patent No.: US 6,348,560 B1
(45) Date of Patent: Feb. 19, 2002

(54) USE OF OLIGOMERIC IODINATED POLYCARBONATES

(75) Inventors: Axel Brenner; Martin Döbler, both of Düsseldorf; Walter Köhler, Duisburg; Siegfried Neumann, Tönisvorst, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/868,205
(22) PCT Filed: Dec. 7, 1999
(86) PCT No.: PCT/EP99/09557
    § 371 Date: Jun. 13, 2001
    § 102(e) Date: Jun. 13, 2001
(87) PCT Pub. No.: WO00/37530
    PCT Pub. Date: Jun. 29, 2000

(30) Foreign Application Priority Data
Dec. 18, 1998 (DE) .......................... 198 58 774

(51) Int. Cl.⁷ ................................. C08G 64/00
(52) U.S. Cl. ....................................... 528/196
(58) Field of Search ........................... 528/196

(56) References Cited

U.S. PATENT DOCUMENTS 4,182,787 A * 1/1980 Goossens et al. ............. 428/36

* cited by examiner

*Primary Examiner*—Terressa M. Boykin
(74) *Attorney, Agent, or Firm*—Joseph C. Gil; James R. Franks

(57) ABSTRACT

A method of using oligocarbonates having terminal groups containing iodine to prepare molded articles (e.g., toys and medical equipment) having high X-ray contrast is described. The oligocarbonates contain more thaan one diol unit, and have a weight average molecular weight (Mw) of less than 3000.

12 Claims, No Drawings

USE OF OLIGOMERIC IODINATED POLYCARBONATES

CROSS REFERENCE TO RELATED PATENT APPLICATIONS

The present patent application claims the right of priority under 35 U.S.C. 119 and 35 U.S.C. 365 of International Application No. PCT/EP99/09557, filed Dec. 7, 1999, which was published in German as International Patent Publication No. WO 00/37530 on Jun. 29, 2000, which is entitled to the right of priority of German Patent Application No. 198 58 774.0, filed Dec. 18, 1998.

FIELD OF THE INVENTION

This invention relates to the use of oligocarbonates having terminal groups containing iodine for moulded articles having high X-ray contrast, in particular for toys and medical accessories.

BACKGROUND OF THE INVENTION

Materials which have as high a transparency as possible and good mechanical properties and can be detected in the body in X-ray examinations are sought for the field of medicine and for children's toys. Unlike metallic articles, as a rule articles made of plastic are not, or only with difficulty, detectable in the X-ray image, particularly behind bones. X-ray contrast can be imparted to such moulding compositions by means of suitable additives.

Transparent plastics moulding compositions made from polycarbonates having terminal groups containing iodine are described in U.S. Pat. No. 3,469,704 and DE-A 17 20 812.

However, the expense of synthesis, especially in the case of polymers having a high molecular weight, can be extremely high and the iodine content attained in the moulding is in some cases low.

In commercially available iodine-containing compounds, problems can arise in connection with the compatibility, the colour fastness and the migration of molecules.

In prior art there is thus to date still no plastics composition available having an adequate X-ray contrast for use as transparent plastics articles, particularly toys and medical accessories.

Owing to its excellent mechanical properties, polycarbonate has long been used in particular for parts of toys which are transparent and subjected to high mechanical stress. It is now intended to develop a type of plastic which can be detected in a conventional X-ray image, with unaltered high transparency and as far as possible only slightly impaired mechanical properties. The layer thickness at which the plastic is still detectable should be as small as possible, but at most 1.2 mm.

SUMMARY OF THE INVENTION

The object was to develop moulding compositions which possess an adequate contrast in X-ray examinations, while having good mechanical properties and transparency. The addition of heavy metals was excluded on toxicological grounds, as materials for children's toys were being sought.

The present application accordingly provides the use of oligocarbonates having terminal groups containing iodine for moulded articles having high X-ray contrast, wherein the oligocarbonates contain more than one diol unit and have a weight average molecular weight Mw of less than 3,000.

DETAILED DESCRIPTION OF THE INVENTION

Mixtures of the iodine-containing compounds specified above with one another and with other iodine-containing substances are possible.

Particularly suitable oligocarbonates are those containing iodinated phenols, such as 2-iodophenol, 3-iodophenol, 4-iodophenol, 2,3-diiodophenol, 2,4-diiodophenol, 2,5-diiodophenol, 2,6-diiodophenol, 3,4-diiodophenol, 3,5-diiodophenol, 2,3,4-triiodophenol, 2,3,5-triiodophenol, 2,3,6-triiodophenol, 2,4,5-triiodophenol, 2,4,6-triiodophenol, 3,4,5-triiodophenol, as well as their alkyl-substituted compounds, as terminal groups. 2,4,6-triiodophenol is a particularly preferred terminal group. All diols mentioned in the present patent for use in polycarbonate are suitable as a diol unit for the iodinated oligocarbonates; 2,2-bis(4-hydroxyphenyl)propane is preferred.

The moulded articles, in particular toys and medical equipment, contain the oligomeric iodine compound in quantities such that the iodine content is from 0.2 to 19.9 wt. %, preferably 0.3 to 15 wt. %, particularly preferably 0.4 to 10 wt. %.

The oligocarbonates having terminal groups containing iodine are generally used in transparent plastics.

The transparent plastics used are preferably transparent thermoplastics, particularly preferably the polymers of ethylenically unsaturated monomers and/or polycondensates of bifunctional reactive compounds.

Particularly suitable plastics are polycarbonates or copolycarbonates based on diphenols. The oligomers according to the invention may also be used, however, with poly- or copolyacrylates and poly- or copolymethacrylates such as, for example, poly- or copolymethyl methacrylate, and also as copolymers with styrene such as, for example, transparent polystyrene-acrylonitrile (SAN).

They may also be incorporated into transparent cycloolefins, poly- or copolycondensates of terephthalic acid such as, for example, poly- or copolyethylene terephthalate (PET or CoPET) or glycol-modified PET (PETG).

The person skilled in the art will achieve excellent results with polycarbonates or copolycarbonates.

Thermoplastic aromatic polycarbonates for the purpose of the present invention are either homopolycarbonates or copolycarbonates; the polycarbonates may, in known manner, be linear or branched.

The oligocarbonates and polycarbonates or copolycarbonates are produced in known manner from diphenols, carbonic acid derivatives, optionally chain stoppers and optionally branching agents.

Details regarding the production of polycarbonates have been set down in many patent specifications for about 40 years. Here reference is made, by way of example, only to Schnell, "Chemistry and Physics of Polycarbonates", Polymer Reviews, Vol. 9, Interscience Publishers, New York, London, Sydney, 1964, to D. Freitag, U. Grigo, P. R. Müller, H. Nouvertne', BAYER AG, "Polycarbonates" in Encyclopedia of Polymer Science and Engineering, Vol. 11, Second Edition, 1988, pages 648–718 and finally, to Dres. U. Grigo, K. Kirchner and P. R. Müller, "Polycarbonates" in Becker/Braun, Kunststoff-Handbuch, Volume 3/1, Polycarbonate, Polyacetale, Polyester, Celluloseester, Carl Hanser Verlag, Munich, Vienna, 1992, pages 117–299.

Suitable diphenols for the production of polycarbonates are, for example, hydroquinone, resorcinol, dihydroxydiphenyls, bis(hydroxyphenyl)alkanes, bis(hydroxyphenyl)cycloalkanes, bis(hydroxyphenyl) sulfides, bis(hydroxyphenyl) ethers, bis(hydroxyphenyl) ketones, bis(hydroxyphenyl) sulfones, bis(hydroxyphenyl) sulfoxides, α,α'-bis(hydroxyphenyl)diisopropylbenzenes, as well as their ring-alkylated and ring-halogenated compounds.

Preferred diphenols are 4,4'-dihydroxydiphenyl, 2,2-bis(4-hydroxyphenyl)propane, 2,4-bis(4-hydroxyphenyl)-2-methylbutane, 1,1-bis(4-hydroxyphenyl)-p-diisopropylbenzene, 2,2-bis(3-methyl-4-hydroxyphenyl)propane, 2,2-bis(3-chloro-4-hydroxyphenyl)propane, bis(3,5-dimethyl-4-hydroxyphenyl)methane, 2,2-bis(3,5-dimethyl-4-hydroxyphenyl)propane, bis(3,5-dimethyl-4-hydroxyphenyl)sulfone, 2,4-bis(3,5-dimethyl-4-hydroxyphenyl)-2-methylbutane, 1,1-bis(3,5-dimethyl-4-hydroxyphenyl)-p-diisopropylbenzene, 2,2-bis(3,5-dichloro-4-hydroxyphenyl)-propane, 2,2-bis(3,5-dibromo-4-hydroxyphenyl)propane and 1,1-bis(4-hydroxyphenyl)-3,3,5-trimethylcyclohexane.

Particularly preferred diphenols are 2,2-bis(4-hydroxyphenyl)propane, 2,2-bis(3,5-dimethyl-4-hydroxyphenyl)propane, 2,2-bis(3,5-dichloro-4-hydroxyphenyl)propane, 2,2-bis(3,5-dibromo-4-hydroxyphenyl)propane, 1,1-bis(4-hydroxyphenyl)cyclohexane and 1,1-bis(4-hydroxyphenyl)-3,3,5-trimethylcyclohexane.

These and other suitable diphenols are described for example in U.S. Pat. Nos. 3,028,635, 2,999,835, 3,148,172, 2,991,273, 3,271,367, 4,982,014 and 2,999,846, in Deutsche Offenlegungsschriften 1 570 703, 2 063 050, 2 036 052, 2 211 956 and 3 832 396, in the French Patent 1 561 518, in the monograph by H. Schnell, "Chemistry and Physics of Polycarbonates", Interscience Publishers, New York, 1964 and in the Japanese published patent applications 62039/1986, 62040/1986 and 105550/1986.

In the case of homopolycarbonates, only one diphenol is used. In the case of copolycarbonates, several diphenols are used.

Examples of suitable carbonic acid derivatives are phosgene or diphenyl carbonate.

Both monophenols and monocarboxylic acids are suitable chain stoppers. Suitable monophenols are phenol itself, alkylphenols, such as cresols, p-tert.-butylphenol, p-n-octylphenol, p-isooctylphenol, p-n-nonylphenol and p-isononylphenol, halophenols such as p-chlorophenol, 2,4-dichlorophenol, p-bromophenol and 2,4,6-tribromophenol, 2,4,6-triiodophenol, p-iodophenol, and mixtures thereof.

A preferred chain stopper is p-tert.-butylphenol.

Suitable monocarboxylic acids are benzoic acid, alkylbenzoic acids and halobenzoic acids.

Preferred chain stoppers are the phenols corresponding to formula (I)

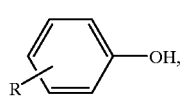

(I)

wherein R is hydrogen, tert. butyl or a branched or unbranched $C_8$- and/or $C_9$-alkyl group.

The quantity of chain stopper to be used is 0.1 mol % to 5 mol %, based on moles of the respective diphenols used. The chain stoppers may be added prior to, during or after the phosgenation.

Suitable branching agents are the trifunctional or more than trifunctional compounds known in polycarbonate chemistry, in particular those having three or more than three phenolic OH groups.

Suitable branching agents are, for example, phloroglucinol, 4,6-dimethyl-2,4,6-tri(4-hydroxyphenyl)-2-heptene, 4,6-dimethyl-2,4,6-tri(4-hydroxyphenyl)heptane, 1,3,5-tri(4-hydroxyphenyl)benzene, 1,1,1-tri(4-hydroxyphenyl)ethane, tri(4-hydroxy-phenyl)phenylmethane, 2,2-bis[4,4-bis(4-hydroxyphenyl)cyclohexyl]propane, 2,4-bis(4-hydroxyphenylisopropyl)phenol, 2,6-bis(2-hydroxy-5'-methylbenzyl)-4-methylphenol, 2-(4-hydroxyphenyl)-2-(2,4-dihydroxyphenyl)propane, hexa(4-(4-hydroxyphenylisopropyl)-phenyl)orthoterephthalate, tetra(4-hydroxyphenyl)-methane, tetra(4-(4-hydroxyphenylisopropyl)phenoxy)methane and 1,4-bis(4',4''-dihydroxytriphenyl)methyl)benzene, as well as 2,4-dihydroxybenzoic acid, trimesic acid, cyanuric chloride and 3,3-bis(3-methyl-4-hydroxyphenyl)-2-oxo-2,3-dihydro-indole.

The quantity of optionally used branching agent is 0.05 mol % to 2 mol %, again based on moles of the respective diphenols used.

The branching agents may either be introduced in the alkaline phase together with the diphenols and the chain stoppers, or added in solution in an organic solvent prior to the phosgenation. In the case of the transesterification process, the branching agents are introduced together with the diphenols.

All these steps in the production of thermoplastic polycarbonates are familiar to the person skilled in the art.

The plastic naturally constitutes the bulk of the compositions, so that as a rule it is present in quantities of between 85.0 and 99.9 wt. %, preferably 90 and 99 wt. %, particularly preferably between 93 and 98 wt. %, of the moulded article.

In an embodiment of the present invention, the moulded article contains, in addition to the oligocarbonates having iodine containing terminal groups, at least one transparent thermoplastic (e.g., a non-halogenated polycarbonate or non-halogenated copolycarbonate) in quantities of 80 to 99.9 wt. % based on the moulded article. The transparent thermoplastic(s) is preferably present in an amount of 85 to 98 wt. %, and particularly preferably in an amount of 90 to 97 wt. %, based on the moulded article.

In a preferred embodiment, the iodine content of the moulding is from 0.2 to 19.9 wt. %, preferably 0.3 to 15 wt. %, particularly preferably 0.4 to 10 wt. %.

But it can also be desirable for the iodine content of the moulding to be from 20.1 to 30 wt. %.

To achieve improved compositions, at least one other additive conventionally present in thermoplastic materials, preferably poly- and copolycarbonates, may in addition be incorporated—such as, for example, stabilisers (as described, for example, in EP 0 839 623 A1 or EP 0 500 496 A1), particularly heat stabilisers, in particular organic phosphites or phosphines, for example, triphenylphosphine; mould release agents, for example, fatty acid esters of glycerol or of tetramethanolmethane, with unsaturated fatty acids also being wholly or partially epoxidisable, in particular glycerol monostearate or pentaerythritol stearate (PETS); flameproofing agents, antistatic agents, UV absorbers, for example, triazoles; fillers, foaming agents, dyes, pigments, optical brighteners, transesterification catalysts and nucleating agents or the like—preferably each in quantities of up to 5 wt. %, preferably 0.01 to 5 wt. %, based on the total mixture, particularly preferably 0.01 to 1 wt. %, based on the quantity of plastic.

Mixtures of these additives are also possible.

Particularly good properties are achieved by using UV stabilisers of the triazole series. Here the following in particular may be mentioned: 2-(3',5'-bis(1,1-dimethylbenzyl)-2'-hydroxyphenyl)benzotriazole, 2-(2'-hydroxy-5'-(tert-octyl)-phenyl)benzotriazole, 2-(2'- hydroxy-3'-(2-butyl)-5'-(tert-butyl)phenyl)benzotriazole, bis(3-(2H-benzotriazolyl)-2-hydroxy-5-tert-octyl)methane, 2-(4-hexoxy-2-hydroxyphenyl)-4,6-diphenyl-1,3,5-triazine, and benzophenones such as, for example, 2,4-dihydroxybenzophenone.

The X-ray opaque polymer compositions thus obtained can be converted into moulded articles such as, for example, parts of toys, as well as fibres, films, tapes, sheets, multi-wall sheets, vessels, tubes and other profiles, by the conventional methods such as, for example, hot pressing, spinning, extrusion or injection moulding. The polymer compositions can also be processed to form cast sheets. Accordingly, the invention also relates to the use of the polymer compositions according to the invention for the production of a moulded article. The use of multilayered systems is also of interest. In this connection, the polymer composition according to the invention having a relatively high content of iodine-containing additives is applied in a thin layer to a moulded article made from a polymer which is X-ray transparent. The application may take place at the same time as or immediately after the shaping of the parent substance, for example, by coextrusion or multicomponent injection moulding. But the application may also be to the finally shaped parent substance, for example, by lamination with a film or by coating with a solution. The moulding compositions are particularly suitable for transparent parts of children's toys or for medical applications. In this connection, such moulded articles are most particularly suitable for small parts of children's toys.

EXAMPLES

Production of the Iodinated Oligocarbonates According to the Invention 161.1 g (0.11 mol) oligo[2,2-bis(4-hydroxyphenyl) propanecarbonate] chloroformic ester (degree of polymerisation approx. 5) was dissolved in 1000 g dichloromethane. A clear solution consisting of 89.1 g (0.189 mol) 2,4,6-triiodophenol, 35.6 g (0.40 mol) 45% sodium hydroxide solution and 800 g water was added at 20° C. to 25° C., with stirring. After 5 minutes, 0.71 g N-ethylpiperidine was added thereto and the mixture was stirred intensively for 30 minutes. The dichloromethane phase was separated from the aqueous phase and washed free from electrolytes. The solvent was evaporated off and the concentrated solution was dried at 120° C. in a water-jet vacuum.

Yield: 202 g of colourless solid

Analyses: phenolic OH: 160 mg/kg, saponifiable Cl:<0.2 mg/kg

Iodine content: approx. 27%

Example 1

94.7 parts polycarbonate (Makrolon 2808®, Bayer AG) was compounded together with 5.9 wt. % of oligocarbonates according to the invention (triiodophenol terminal groups) and 0.5 wt. % of mould release agent PETS at 280° C. by means of a twin-screw extruder and then injection-moulded to form test rods of various thicknesses. The properties of these mouldings are listed in Table 1.

Table 1

Modulus of elasticity: 2500 N/mm$^2$

Elongation at tear: 119%

$T_g$=143° C.

Iodine content of the moulding: 1.6%

Test rod of 1.2 mm in thickness: detectable by X-rays

Test rod of 1.6 mm in thickness: detectable by X-rays

Test rod of 2.4 mm in thickness: detectable by X-rays

Test rod of 3.2 mm in thickness: detectable by X-rays

The detectability by X-rays was within the limits conventional in the field of medicine.

The transparency of these mouldings was in each case more than 85%. Even when containing 85 wt. % of polycarbonate, 14.5 wt. % of oligomer according to the invention (triiodophenol terminal groups) and 0.5 wt. % of mould release agent PETS, the test rods are still completely transparent.

These mouldings can therefore be detected in the human body, even in the shadows cast by bones, in a conventional medical X-ray examination.

The addition of iodine compounds of low molecular weight brings about a plasticisation of the material. This is detectable from the decreased glass point and from the lower solution viscosity. The high glass transition temperature $T_g$ in Example 1, however, remains virtually unaltered, so that a high heat deflection temperature is maintained.

What is claimed is:

1. A method of using oligocarbonates having terminal groups containing iodine to prepare moulded articles having high X-ray contrast, wherein the oligocarbonates contain more than one diol unit and have a weight average molecular weight Mw of less than 3,000.

2. The method of claim 1 wherein the moulded articles further contain at least one transparent thermoplastic in quantities of 80 to 99.9 wt. %, based on the moulded article.

3. The method of claim 1 wherein the iodine content of the moulding is from 0.2 to 19.9 wt. %.

4. The method of claim 1 wherein the iodine content of the moulding is from 20.1 to 30 wt. %.

5. A toy containing oligocarbonates having terminal groups containing iodine wherein the oligocarbonates contain more than one diol unit and have a weight average molecular weight Mw of less than 3,000 said toy having high X-ray contrast.

6. Medical equipment containing oligocarbonates having terminal groups containing iodine wherein the oligocarbonates contain more than one diol unit and have a weight average molecular weight Mw of less than 3,000, the medical equipment having high X-ray contrast.

7. The method of claim 2 wherein the transparent thermoplastic is selected from at least one of non-halogenated polycarbonate and non-halogenated copolycarbonate.

8. The method of claim 2 wherein the transparent thermoplastic is present in an amount of 85 to 98 wt. %, based on the moulded article.

9. The method of claim 2 wherein the transparent thermoplastic is present in an amount of 90 to 97 wt. %, based on the moulded article.

10. The method of claim 3 wherein the iodine content of the moulding is from 0.3 to 15 wt. %.

11. The method of claim 3 wherein the iodine content of the moulding is from 0.4 to 10 wt. %.

12. The method of claim 1 wherein the iodine containing terminal groups of said oligocarbonates are residues of iodinated phenols selected from at least one of 2-iodophenol, 3-iodophenol, 4-iodophenol, 2,3-diiodophenol, 2,4-diiodophenol, 2,5-diiodophen-ol, 2,6-diiodophenol, 3,4-diiodophenol, 3,5-diiodophenol, 2,3,4-triiodophen-ol, 2,3,5-triiodophenol, 2,3,6-triiodophenol, 2,4,5-triiodophen-ol, 2,4,6-triiodo-phenol and 3,4,5-triiodophenol.

* * * * *